Figure 1:
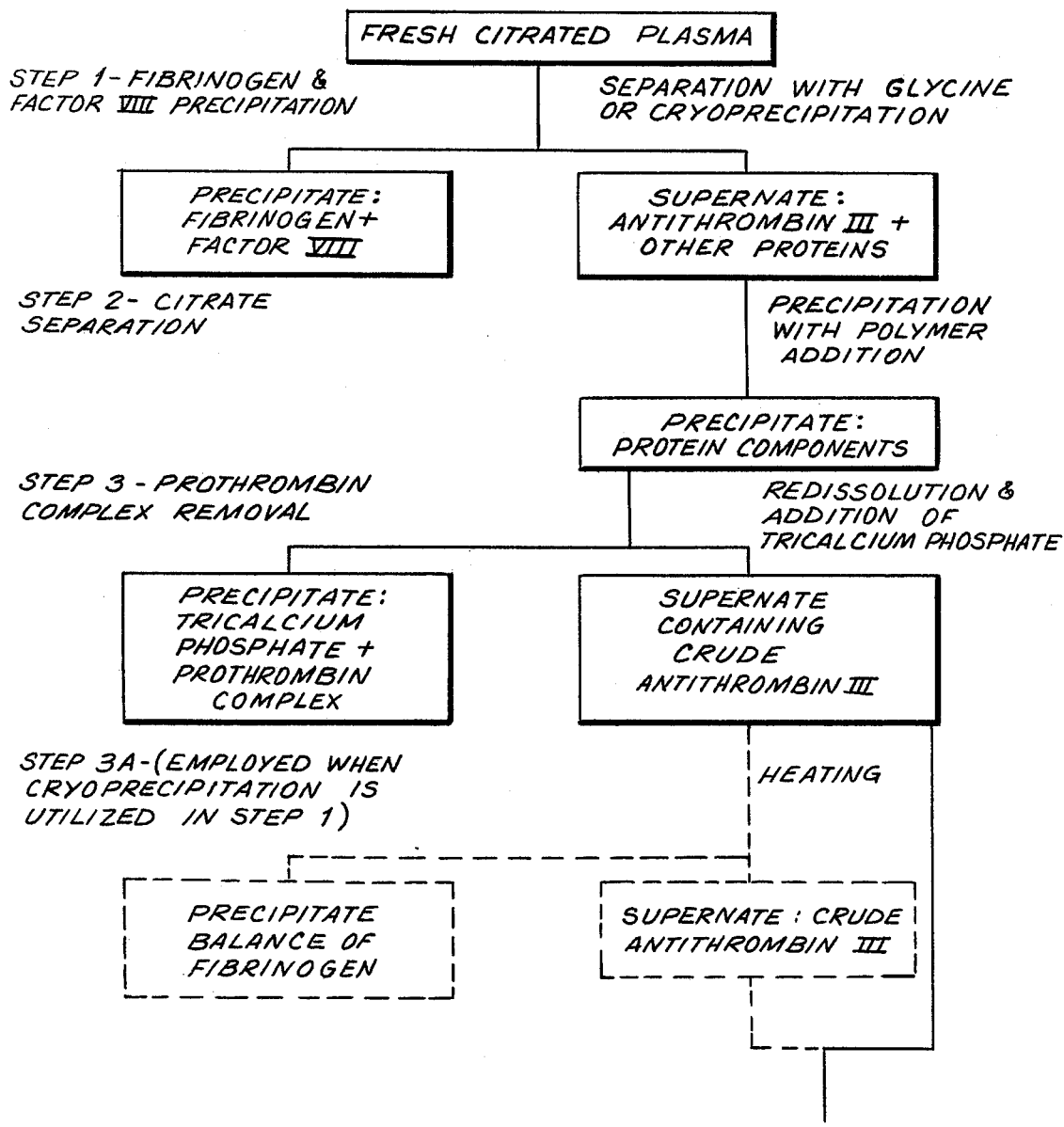

United States Patent [19]

Bick et al.

[11] 4,087,415

[45] May 2, 1978

[54] ANTITHROMBIN III

[75] Inventors: Rodger L. Bick, Los Angeles; Lajos F. Fekete, Costa Mesa, both of Calif.

[73] Assignees: William L. Wilson; Rodger L. Bick; Lajos F. Fekete, all of Santa Monica, Calif.

[21] Appl. No.: 694,167

[22] Filed: Jun. 9, 1976

[51] Int. Cl.² ............................................. A23J 1/06
[52] U.S. Cl. ....................... 260/112 B; 210/DIG. 23; 424/101; 424/177
[58] Field of Search .................... 260/112 B; 424/101; 210/DIG. 23

[56] References Cited

U.S. PATENT DOCUMENTS

| | | | |
|---|---|---|---|
| 3,631,018 | 12/1971 | Shanbrom et al. | 260/112 B |
| 3,682,881 | 8/1972 | Fekete et al. | 260/112 B |
| 3,770,631 | 11/1973 | Fekete et al. | 260/112 B X |
| 3,839,314 | 10/1974 | Fekete et al. | 424/101 X |
| 3,842,061 | 10/1974 | Andersson et al. | 260/112 B |
| 3,850,903 | 11/1974 | Garcia et al. | 260/112 B |
| 3,880,989 | 4/1975 | Garcia | 260/112 B X |
| 3,956,259 | 5/1976 | Garcia et al. | 260/112 B |

OTHER PUBLICATIONS

Machovich et al., *Thrombosis Research*, 7, pp. 305-313 (1975).
Wagner et al., "Precipitation of Factor VIII with Aliphatic Amino Acids", *The Hemophilias International Symposium* (1964) pp. 81-86.
Abilgaard, *Chemical Abstracts*, vol. 67: 78,954s (1967).

*Primary Examiner*—Walter C. Danison
*Attorney, Agent, or Firm*—Hubbell, Cohen, Stiefel & Gross

[57] ABSTRACT

High purity antithrombin III is recovered from a procedure in which the other protein fractions in human blood plasma are recovered for further processing. The protein fractions are recovered sequentially in separate steps: fibrinogen and Factor VIII are recovered as a precipitate; prothrombin complex is recovered on the surface of finely divided tricalcium phosphate; albumin and gamma globulin are recovered in an aqueous supernate; a protein precipitate containing lipids, lipoproteins and other trace protein contaminants is recovered; and antithrombin III is recovered as a precipitated phase. The fibrinogen, Factor VIII, prothrombin complex, albumin, gamma globulin and protein contaminants are all recovered in such a way that they are suitable for further processing.

4 Claims, 2 Drawing Figures

ANTITHROMBIN III

Previously, considerable difficulty had been experienced in fractionating blood plasma in such a way as to recover the separate protein fractions without at some point in the procedure sacrificing one or more fractions in order to recover some other fraction. Excessive quantities of blood plasma were required to produce the necessary purified end products. Prior procedures in general were not satisfactory for the commercial production of antithrombin III. Prior procedures often did not produce products that were suitable for clinical use because of the use of reagents or procedures that are unacceptable for clinical products.

In general, the present invention includes a procedure whereby clinically usable antithrombin III is recovered from human blood plasma in a very efficient operation wherein the other protein fractions present in the original plasma are also recovered in usable form.

Figure 2:
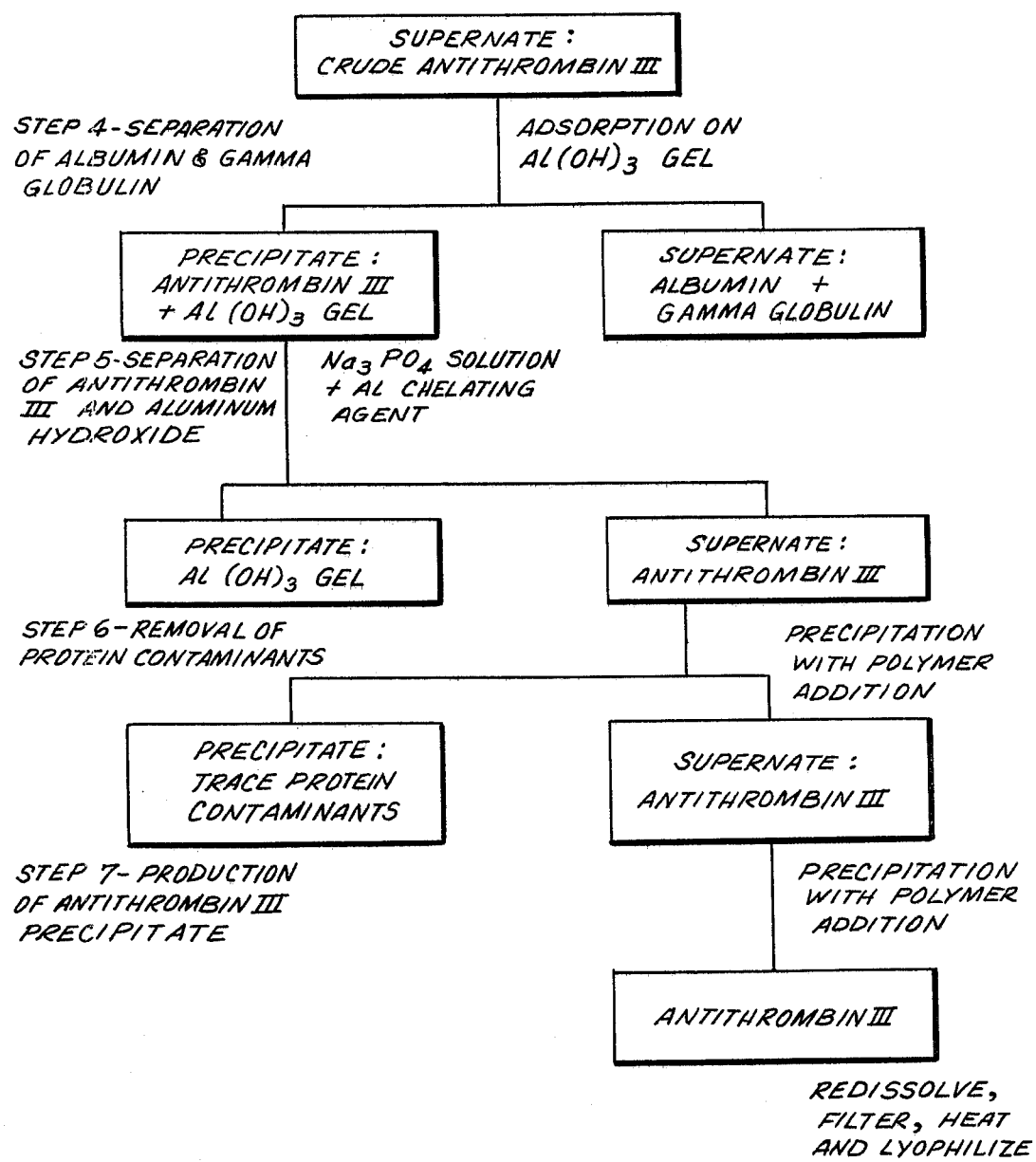

The invention will be more fully understood with reference to the accompanying schematic drawing illustrating a preferred embodiment thereof, in which:

FIG. 1 is a flow diagram showing the initial steps in the preparation of antithrombin III from fresh citrated blood plasma in accordance with the process hereof; and FIG. 2 is a flow diagram similar to FIG. 1, illustrating the further steps of the process.

According to one preferred procedure, fibrinogen and Factor VIII are precipitated from fresh citrated human blood plasma in an initial separation step (see FIG. 1, step 1) with the antithrombin III and other protein materials remaining in the supernate. This initial step is remotely related to steps which have been previously described in the context of other procedures, for example, *The Hemophilias International Symposium*, Washington 1964, Kenneth M. Brinkhous, Editor, 81-86; Shambrom et al U.S. Pat. No. 3,631,018, and Fekete et al. U.S. Pat. No. 3,770,631. Alternatively, the fresh citrated blood plasma is subjected to a cryoprecipitation procedure to remove the fibrinogen and Factor VIII. The precipitated fibrinogen and Factor VIII which are recovered from either procedure are suitable for further processing to recover these valuable materials.

In a second separative step (FIG. 1, step 2) the supernate is admixed with a reagent to cause the precipitation of the protein materials, including the antithrombin III, in the form of a paste. The citrate and other soluble materials are discarded with the supernate. This second separative step is remotely related to those previously described in the context of other procedures, for example, Fekete et al U.S. Pat. Nos. 3,770,631 and 3,839,314.

The protein rich paste from the second separative step is redissolved in a third step (FIG. 1, step 3) and prothrombin complex is separated by the addition of finely divided solid tricalcium phosphate. The prothrombin complex which is separated with the solid phase tricalcium phosphate is suitable for further processing. The procedure of this third step is remotely related to steps described previously with regard to other procedures, for example, *Human Blood Coagulation, Haemostasis and Thrombosis*, 1972, Rosemary Biggs, Editor, 258; Fekete U.S. Pat. Nos. 3,682,881, 3,560,475, 3,770,631, and 3,839,314.

If cryoprecipitation procedures are used in an initial fibrinogen and Factor VIII separation step, the supernate from the third step is heated at about 56 degrees centigrade for approximately five minutes to cause complete separation of the fibrinogen (FIG. 1, step 3A). This heating step is carried out before the fourth step is undertaken.

The supernate from the third step, or the supernate which has been heated for finaL fibrinogen removal, is admixed with aqueous aluminum hydroxide gel (FIG. 2, step 4) to effect the separation of crude antithrombin III with the gel. Albumin and gamma globulin are left in the supernate and are suitable for further processing. This fourth step is remotely related to steps which had been previously described with reference to different procedures, for example, A. Hensen, E. A. Loelinger, *Antithrombin III, Its Metabolism and Its Function in Coagulation*, Thromb. Diather. Haemorrhag. (Sturttg.) 9:Supplement 1 (1963), 210.

Antithrombin III is separated from the aluminum hydroxide gel by contacting the gel with an aqueous solution of sodium phosphate (FIG. 2, step 5). A trace amount of an aluminum chelating agent is provided so as to bind the trace amounts of aluminum ions which are present in the aqueous solution. The spent aluminum hydroxide is discarded and the antithrombin III containing supernate is retained and subjected to a sixth separative step.

In the sixth separative step (FIG. 2, step 6) a moderate amount of reagent is added to cause the precipitation of tace protein contaminants precipitate and are separated from the antithrombin III supernate.

The concentration of the reagent in the supernate is increased in the seventh step (FIG. 2, step 7) so that the antithrombin III is caused to precipitate. The supernate is discarded and the antithrombin III rich precipitate is redissolved in citrated saline, subjected to millepore filtration, heated at about 56 degrees centigrade for approximately 60 hours to destroy any hepatitis associated antigen which may be present, placed in vials, and lyophilized for purposes of storage and transportation.

Alternatively, Cohn IV (IV-1, IV-1+IV-4) paste is used as the feed stock for step 3. The use of the Cohn IV paste as the feed stock for step 3 provides an alternative to carrying out steps 1 and 2, as described hereinabove.

The ionic concentration throughout the first four separative steps is preferably maintained at approximately physiological values, for example, from about 0.13 to 0.16 and preferably about 0.15 molar sodium chloride so as to avoid subjecting the clotting proteins to abnormal salt concentrations which might tend to impair their potency.

Each of the separative steps results in the production of a supernate and a precipitate of some character. The admixture which occurs in each step should be stirred for a minimum of at least about 15 minutes, and where reagents are present in steps two, six and seven, for a minimum of about 30 minutes so as to accomplish thorough intermixing. The length of time for which the admixtures are stirred in each step is generally not critical so long as thorough mixing is accomplished. Mixing in the third step where solid phase tricalcium phosphate is present should not be prolonged beyond approximately 60 minutes because it tends to impair the potency of the antithrombin III.

Phase separation is accomplished in each step by the application of centrifugal force to the aqueous admixtures. In general, approximately 15 minutes at 5,000 gravities is sufficient to effect complete separation; however, longer times may be employed if desired, except that the centrifuging time in the thord step wherein tricalcium phosphate is present should not be unduly extended beyond approximately 30 minutes. The temperature of the aqueous supernates in the second and subsequent steps may conveniently be maintained at approximately room temperature, for example, from about 18° to 30° and preferably about 22°, although higher and lower temperatures from about 0° to 39° centigrade may be employed if desired. Temperatures in excess of about 30 degrees centigrade tend to impair the potency of the clotting factors if the aqueous supernates are maintained at these temperatures for extended periods of time. Temperatures below about 18 degrees centigrade generally require special cooling equipment and procedures which are cumbersome and unnecessary.

The reagents which are used to accomplish the precipitation of various protein fractions in the second, sixth, and seventh steps are preferably block copolymers which are polyoxyethylene-polyoxypropylene condensation products. The quantities of polymer which are used to effect precipitation of the desired protein fraction are somewhat dependent upon temperature with the concentration required to effect precipitation being increased as temperature increases. In steps two and seven complete precipitation of all the protein material which is present in the supernate is desired. In general, at approximately room temperature approximately 20 percent on a weight per volume basis of the polymer is required to effect complete precipitation. At 0° the quantity required to effect complete precipitation is at least approximately 9 percent and at 39° centigrade the quantity required to effect complete separation is approximately at least 28 percent. In general, as the molecular weight of any given polymer increases the quantity of that polymer which is required to effect complete separation of all the protein material is slightly reduced. In step six where it is desired to precipitate trace protein contaminants without precipitating antithrombin III the concentration of polymer should be approximately 12 percent on a weight per volume basis at approximately room temperature, approximately 7 percent at about 0° centigrade and approximately 15 percent at about 39° centigrade. In general, concentrations of from about 10 to 14 percent at approximately room temperature are utilized with a concentration of about 10 to 12 percent being preferred. At these concentrations no significant amount of the antithrombin III is caused to precipitate.

Protein precipitating reagents which have been found to be particularly useful in the procedures of steps two, six, and seven are conveniently prepared by condensing ethylene oxide and propylene oxide polymer to produce a block copolymer. The resultant condensation products are well known materials which can be represented by the following structural formula:

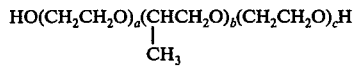

wherein a and c represent the number of oxyethylene units, and b represents the number of oxypropylene units in the block copolymer. Block copolymers which are suitable for these purposes are available from Wyandotte Chemicals Corp. under the designations "Pluronic F-38" and "Pluronic F-68." The Pluronic F-38 material contains about 80 percent polyoxyethylene units and the polyoxypropylene polymer portion of the molecule has a molecular weight of about 950. The condensation product has a molecular weight of about 4,750. The Pluronic F-68 material also contains about 80 percent polyoxyethylene units and the polyoxypropylene polymer portion of the molecule has a molecular weight of about 1,750 with the total molecular weight of the condensation product being about 8,750. In general these block copolymers contain at least about 50 percent ethylene oxide units in the molecule, and the polyoxypropylene polymer portion of the molecule has a molecular weight of at least about 900. The block copolymers must be water soluble at concentrations of at least about 20 percent on a weight per volume basis at temperature of from abount 10 degrees to 35 degrees centigrade. These materials must be nontoxic.

A less satisfactory but acceptable protein precipitating reagent which may be used to accomplish the protein precipitation of steps two, six, and seven is polyethylene glycol. Polyethylene glycol having a molecular weight of from about 4,000 to 6,000 is suitable for use in the protein precipitaion steps two, six, and seven.

The first step in the separation procedure is conveniently accomplished by admixing fresh citrated human blood plasma containing all of its normal protein constituents with from about 1.7 to 2.3 and preferably about 1.8 moles of glycine at a temperature of about 8 degrees centigrade and a pH of from about 6.7 to 7.0 and preferably about 6.88. When cryoprecipitation procedures are used, the conventional freezing and thawing procedures are used.

The supernate from the first step in diluted with saline to at least 2 and preferably 3 times the original plasma volume and is admixed in the second step with a sufficient amount of polymer to cause the precipitation of all of the protein in that supernate, and the pH is adjusted to a value from about 5.5 to 7.5 and preferably about 6.5.

The solid phase protein precipitate from the second step is redissolved in the third step in an amount of aqueous saline solution sufficient to bring its volume back to approximately the original plasma volume; the pH of the resultant admixture is adjusted to a value of from about 7.0 to 7.3 and preferably about 7.2; the ionic strength is adjusted to approximately physiological value and at least about 0.5 percent, on a weight per volume basis, and preferably at least about 1 percent of tricalcium phosphate is added. Quantities in excess of one percent may be used if desired.

The supernate from the prothrombin complex separation step three is admixed with aluminum hydroxide gel in an amount of from about 1/10th to ⅓rd and preferably approximately ⅓rd the original volume of the plasma raw material. The aluminum hydroxide gel is an aqueous gel containing about 2 percent by weight of aluminum hydroxide. The pH is adjusted to a value of from about 6.6 to 6.9 and preferably about 6.75.

The resultant antithrombin III containing aluminum hydroxide gel is contacted in the fifth step with from approximately 1/10th to ⅓rd the original volume of the plasma raw material of water, the quantity being established by the dictates of convenience and handling requirements. The pH is adjusted to a value of from about 7.6 to 7.9 and preferably about 7.8. Sodium phosphate in the amount of from about 0.36 to 1.0 and preferably about 0.37 moles is provided in the aqueous admixture to cause the separation of the antithrombin III from the aluminum hydroxide gel. A chelating agent, for example, ethylene diamine tetraacetic acid is included in the admixture in an amount of from abount 0.0001 to 0.004 moles and preferably about 0.003 moles for the purpose of chelating with the trace amounts of aluminum which are present in the supernate.

The antithrombin III containing supernate from the fifth step is adjusted to a pH value of from about 5.5 to 7.5 and preferably about 5.5 and an amount of polymer sufficient to precipitate the small amounts of protein contaminants which are present in this antithrombin III rich-protein lean supernate is added. The only protein remaining in the supernate from this sixth step is antithrombin III. The concentration of the polymer in this supernate is increased to a value sufficient to cause the precipitation of all of the antithrombin III.

The fibrinogen and Factor VIII precipitate which is recovered in step one, and prothrombin complex which is recovered in step three, and the albumin and gamma globulin which are recovered in step four are suitable for further processing to isolate and recover these valuable fractions. The trace protein contaminants in step six are recoverable if desired.

The steps of this procedure are independent of one another in that the raw material for any one of the steps two through seven may be produced by a procedure which is different from that of the preceding steps provided only that the raw material for the step in question has about the same characteristics as those provided by the above described sequence of steps. For example, any raw material which contains antithrombin III and prothrombin complex but which is free of fibrinogen, Factor VIII, and citrate may be used as the raw material for step three. Likewise a raw material which is free of fibrinogen, Factor VIII and prothrombin complex may be used as a raw material for step four. A raw material which is free of fibrinogen, Factor VIII, prothrombin complex, albumin, and gamma globulin may be used as the raw material for step five and so on for steps six and seven.

The yield of antithrombin III is approximately 75 percent and the resulting concentrated product is of a very high purity. The potency per unit volume of the final product is controlled by the quantity of citrated saline which is used in redissolving the precipitated antithrombin III product of step seven, any may be as much as 20 times that of the plasma raw material.

The procedures of this invention are applicable to a wide variety of plasmas including fresh plasma, concentrated plasma, reconstituted cryoprecipitate Cohn fractions and the like.

The reagents used throughout this procedure are nontoxic and generally recognized to be acceptable for clinical use. The reagents are such that they do not substantially impair the potency of any of the factors. The conditions throughout are such that the potencies of the various factors are not substantially impaired. the procedure accomplishes the necessary separation and purification steps without sacrificing one fraction in order to recover another, thus conserving a scarce and precious raw material.

The following example is submitted to illustrate and not to limit the invention. All parts and percentages are on a weight per volume basis unless otherwise indicated.

EXAMPLE

The purpose of this example is to illustrate the sequential preparation of high potency, high purity antithrombin III from fresh citrated human blood plasma by a procedure which does not destroy any of the plasma fractions and is suited for use on a commercial scale.

The pooled human blood plasma raw material which was used in this example was fresh, citrated, and unconcentrated. One liter of this material was selected as the raw material for this procedure. Sodium citrate was present in the quantity of 0.02 moles.

STEP 1 — FIBRINOGEN AND FACTOR VIII PRECIPITATION

The pH of the human blood plasma raw material was adjusted with one normal acetic acid to a value of 6.88 and the temperature was brought to 8° centigrade. 1.8 moles of glycine was added and the resultant admixture was sitrred for about 45 minutes. The admixture was then centrifuged for about 15 minutes, and the fibrinogen-Factor VIII precipitate was separated by decantation.

STEP 2 — CITRATE SEPARATION

The supernate from step one was treated with one normal acetic acid to reduce the pH to a value of 6.5; sodium chloride solution (0.15 molar) was added in twice the volume of the fibrinogen-Factor VIII free supernate; the temperature was allowed to rise to about 22 degrees centigrade; and 25 percent (grams per 100 milliliters) of a block copolymer was added to the supernate. The supernate was stirred for about 15 minutes and centrifuged at 5,000 gravities for an additional 15 minutes. All of the protein constituents in the supernate were found in the resultant precipitate. The citrate containing supernate was discarded. The block copolymer was an ethylene oxide-propylene glycol condensation product in which about 80 percent of the block copolymer consisted of polyoxyethylene units. the polyoxypropylene portion of the polymer had a molecular weight of about 1,750. The total molecular weight of the copolymer was about 8,750. This material is available commercially from Wyandotte Chemicals Corp. under the designation "Pluronic F-68."

Repetition of this step utilizing 25 percent (grams per 100 milliliters) of a lower molecular weight block copolymer which is identified by the brand name "Pluronic F-38," and described hereinabove produces satisfactory separation.

Repetition of this second step utilizing 25 percent (grams per 100 milliliters) of polyethylene glycol having a molecular weight of 4,000 likewise results in a satisfactory separation.

STEP 3 — PROTHROMBIN COMPLEX REMOVAL

The protein precipitate from step two was redissolved in normal saline to a volume of about 1 liter; the pH was adjusted to a value of 7.2; and 1 gram percent (grams per 100 milliliters) of finely divided tricalcium phosphate was added. The tricalcium phosphate did not dissolve to any significant extent. The admixture was stirred for about 45 minutes and centrifuged thereafter for about 15 minutes at 5,000 gravities. The solid phase tricalcium phosphate contains the prothrombin complex which was initially present in the blood plasma. The supernate and solid phase precipitate were separated. The pH in step three was adjusted with one normal sodium hydroxide to a value of about 7.2.

Repetition of this step 3 utilizing Cohn IV-1 paste as the starting material for this step results in the production of a satisfactory supernate and solid phase precipitate. Likewise, the use of Cohn IV-1+IV-4 paste as the raw material for this step 3 results in a satisfactory supernate and solid phase precipitate.

The effectiveness and completeness of the separation in step three depends in significant part upon the complete removal of citrate in step two. The use of triple dilution with saline solution in step two enhances the effectiveness of the citrate separation step.

STEP 4 — SEPARATION OF ALBUMIN AND GAMMA GLOBULIN

An aqueous aluminum hydroxide gel containing about 2.0 gram percent aluminum hydroxide was admixed with the supernate from step three. About 300 milliliters of aluminum hydroxide gel was admixed with the one liter of supernate. The pH was adjusted to a value of about 6.75. The admixture was stirred for about 30 minutes and thereafter centrifuged at about 5,000 gravities for a period of 15 minutes. The albumin and gamma globulin remained in the aqueous supernate, and the antithrombin III was combined with the aluminum hydroxide gel. The antithrombin III rich gel and the supernate were separated.

STEP 5 — SEPARATION OF ANTITHROMBIN III AND ALUMINUM HYDROXIDE

About 300 milliliters of water containing 0.37 moles of sodium phosphate and 0.003 moles of ethylene diamine tetraacetic acid was admixed with the antithrombin III rich aluminum gel from step four and the pH was adjusted to a value of about 7.8. The admixture was stirred for about 15 minutes, and was thereafter centrifuged at about 5,000 gravities for about 15 minutes. The depleted aluminum hydroxide gel was separated from the antithrombin III rich supernate and was discarded.

STEP 6 — REMOVAL OF PROTEIN CONTAMINANTS

The 300 milliliter volume of supernate from step five was brought to a pH of 5.5 by the addition of 1 normal acetic acid and about 12 gram percent of "Pluronic F-68" was added to the supernate. The admixture was stirred for about 45 minutes and therafter centrifuged at 5,000 gravities for about 15 minutes. The precipitate of protein contaminants including lipids and lipoproteins was removed from the antithrombin III rich supernate.

STEP 7 — PRODUCTION OF ANTITHROMBIN III PRECIPITATE

The 300 milliliter volume of supernate from step six was combined with additional "Pluronic F-68" to provide a total concentratin of 20 gram percent. The resultant admixture was stirred for about 45 minutes and thereafter centrifuged at 5,000 gravities for about 15 minutes. The antithrombin III values were recovered in the solid phase paste.

Repetition of steps six and seven utilizing "Pluronic F-38" in concentrations of 12 gram percent and 20 gram percent, respectively, results in the production of an antithrombin III rich solid phase paste as the product of step seven. Likewise, repetition of steps six and seven utilizing polyethylene glycol having a molecular weight of about 4,000 in concentrations of about 12 gram percent and 20 gram percent, respectively, results in the producton of a high purity antithrombin III containing paste in step seven.

Throughout steps two through seven the temperature was maintained at approximately 22°. Throughout steps two through four the saline content was maintained at about 0.15 molar sodium chloride.

The solid phase antithrombin III product obtained from step seven was redissolved citrated saline containing 1 part by volume of 0.1 molar sodium citrate and 4 parts by volume of 0.15 molar sodium chloride. The redissolved high purity, high potency antithrombin III product was millepore filtered and heated at 56 degrees centigrade for 60 hours to remove any hepatitis associated antigen. Antithrombin III is heat stable so that its potency was not destroyed by this heating. The resultant antithrombin III product was placed in vials and lyophilized for storage and transportation. The resultant lyophilized product upon reconstitution is suitable for clinical use.

The yield of antithrombin III recovered from the practice of the hereinabove described seven steps was approximately 75 percent. All of the crude protein fractions which were removed in steps one, three, and four were recovered in high yields and were suitable for further processing and purification. The proteins recovered in step six were suitable for further processing and purification if desired.

What is claimed is:

1. A process for recovering clinically usable antithrombin III comprising:
   (a) admixing a blood plasma fraction which is substantially free of fibrinogen, Factor VIII and prothrombin complex with aqueous aluminum hydroxide gel to adsorb crude antithrombin III on the gel;
   (b) treating the crude antithrombin III-containing aluminum hydroxide gel with a sodium phosphate solution containing an aluminum chelating agent to separate the crude antithrombin III in the supernate remaining therefrom;
   (c) treating said supernate with an ethylene oxide-propylene oxide block copolymer or polyethylene glycol protein precipitating agent to separate purified antithrombin III in the supernate remaining therefrom; and
   (d) separating and recovering the thus purified antithrombin III.

2. The process of claim 1, wherein the purified antithrombin III-containing supernate from step (c) is
   (d) treated with an additional amount of an ethylene oxide-propylene oxide block copolymer or polyethylene glycol protein precipitating agent to precipitate the antithrombin III therefrom.

3. The process of claim 1, wherein the plasma fraction treated in step (a) is prepared by admixing a plasma fraction which is substantially free of fibrinogen and Factor VIII with tricalcium phosphate to precipitate prothrombin complex therefrom, and treating the resulting supernate as set forth in step (a).

4. The process of claim 1, wherein the plasma fraction treated in step (a) is prepared by (i) dissolving a Cohn plasma Fraction IV and (ii) admixing the resulting solution with tricalcium phosphate to precipitate prothrombin complex therefrom, prior to treating the resulting supernate as set forth in step (a).

* * * * *